US00PP23908P2

(12) United States Plant Patent
Smith

(10) Patent No.: US PP23,908 P2
(45) Date of Patent: Sep. 17, 2013

(54) ***CHRYSANTHEMUM* PLANT NAMED 'CIFZ0024'**

(50) Latin Name: *Chrysanthemum×morifolium*
Varietal Denomination: CIFZ0024

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 66 days.

(21) Appl. No.: 13/385,223

(22) Filed: Feb. 8, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — Joshua L. Price

(57) ABSTRACT

A new *Chrysanthemum* plant named 'CIFZ0024' particularly distinguished by the small to medium sized decorative inflorescences, darker yellow-green foliage, medium ball-shaped plant habit, with a natural flowering season response of mid-September.

1 Drawing Sheet

Latin name of the genus and species of the plant claimed: *Chrysanthemum×morifolium.*

Varietal denomination: 'CIFZ0024'.

BACKGROUND OF THE NEW PLANT

The present invention comprises a new *Chrysanthemum*, botanically known as *Chrysanthemum×morifolium*, and hereinafter referred to by the variety name 'CIFZ0024'.

'CIFZ0024' is a product of a planned breeding program. The new cultivar has small to medium sized decorative inflorescences, darker yellow-green foliage, medium ball-shaped plant habit, with a natural flowering season response of mid-September.

'CIFZ0024' originated as a natural whole plant mutation of an unnamed sport of 'Yojacqueline'. 'CIFZ0024' was discovered and selected by the inventor as a single flowering plant within a large population of the parent cultivar grown massed in pots outdoors in a controlled breeding program in Alva, Fla. in March 2009. The parent cultivar has a light yellow inflorescences color, a little larger plant size, and a little slower natural flowering season then 'CIFZ0024'.

The first act of asexual reproduction of 'CIFZ0024' was accomplished when vegetative cuttings were propagated from the initial selection in May 2009 in a greenhouse in Alva, Fla.

BRIEF SUMMARY OF INVENTION

Horticultural examination of plants grown from cuttings of the plant initiated in May 2009, and continuing thereafter, has demonstrated that the combination of characteristics as herein disclosed for 'CIFZ0024' are firmly fixed and are retained through successive generations of asexual reproduction.

'CIFZ0024' has not been observed under all possible environmental conditions. The phenotype may vary significantly with variations in environment such as temperature, light intensity, and day length.

Plant Breeder's Rights for this cultivar were applied for in Canada on Feb. 24, 2011, No. 11-7184 and at the Community Plant Variety Office on Mar. 30, 2011, No. 2011/0795.

'CIFZ0024' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0024' with colors being as true as possible with an illustration of this type.

The photographic drawing shows a flowering potted plant of the new variety and a close-up of the inflorescences.

DETAILED BOTANICAL DESCRIPTION

The plant descriptions, measurements and aforementioned photographs were taken outdoors in Gilroy, Calif. in early August 2011. The plants were growing in an outdoor potted plant trial in one gallon pots in full sun. These plants were approximately 9-10 weeks of age.

Color references are made to The Royal Horticultural Society Colour Chart (R.H.S.) 2001.

TABLE 1

DIFFERENCES BETWEEN THE NEW VARIETY 'CIFZ0024' AND A MOST SIMILAR VARIETY

| | 'CIFZ0024' | 'Synjac Yel' (U.S. Ser. No. 12/925,209, abandoned ) |
|---|---|---|
| Inflorescence color: | Richer yellow | Lighter yellow |
| Stem length: | Longer | Shorter |
| Peduncle length: | Longer | Shorter |
| Disc floret quantity: | Few more | Few less |

Plant:

*Form, growth and habit.*—Herbaceous garden-type, stems upright and outwardly spreading, freely branching.

*Plant height.*—20.0 cm.

*Plant height* (*inflorescence included*).—24.0 - 25.0 cm.
*Plant width.*—34.0-37.0 cm.

Roots:
*Number of days to initiate roots.*—About 4 days at about 22 degrees C.
*Number of days to produce a rooted cutting.*—4-6 days at 22 degrees C.
*Type.*—Fine, fibrous, free branching.
*Color.*—RHS N155B but whiter.

Foliage:
*Arrangement.*—Alternate.
*Immature, leaf color, upper surface.*—Closest to RHS 147A but darker.
*Lower surface.*—RHS 147B but more green.
*Mature, leaf color, upper surface.*—Closest to RHS 147A but darker.
*Lower surface.*—RHS 147B but more green.
*Length.*—2.5-3.2 cm.
*Width.*—2.1-2.5 cm.
*Shape.*—Ovate.
*Base shape.*—Attenuate.
*Apex shape.*—Acute.
*Margin.*—Irregularly incised or partly cleft; entire.
*Texture, upper surface.*—Bifid T-shaped hairs.
*Lower surface.*—Bifid T-shaped hairs.
*Color of veins, upper surface.*—RHS 138A basally, becoming indistinct.
*Color of veins, lower surface.*—RHS 138A basally, becoming indistinct.
*Petiole color.*—RHS 138A.
*Length.*—0.6-1.0 cm.
*Diameter.*—0.15-0.2 cm.
*Texture.*—Bifid T-shaped hairs.

Stem:
*Quantity of main branches per plant.*—About 7.
*Color of stem.*—Closest to RHS 137A.
*Length of stem.*—About 15.0-17.0 cm.
*Diameter.*—0.25-0.3 cm.
*Length of internodes.*—1.0-2.0 cm.
*Texture.*—Bifid T-shaped hairs.
*Color of peduncle.*—Closest to RHS 137A.
*Length of peduncle.*—9.5-10.0 cm.
*Peduncle diameter.*—0.15 cm.
*Texture.*—Bifid T-shaped hairs.

Inflorescence:
*Type.*—Compositae, solitary decorative-type inflorescences, borne terminally above foliage, ray florets arranged acropetally on a capitulum.
*Quantity of inflorescences per plant.*—About 110 with approximately 50-75 buds.
*Lastingness of individual blooms on the plant.*—About 6 weeks from the first color showing.
*Fragrance.*—Slightly spicy.

Bud (just when opening/showing color):
*Color.*—RHS 5C with RHS 13C toward the apex.
*Length.*—0.5-1.2 cm.
*Width.*—0.9-1.2 cm.
*Shape.*—Oblate.

Immature inflorescence:
*Diameter.*—3.8-4.0 cm.
*Color of ray florets, upper surface.*—RHS 6A to RHS 6B.
*Lower surface.*—RHS 7D.

Mature inflorescence:
*Diameter.*—5.2-5.6 cm.
*Depth.*—1.5 cm.
*Total diameter of disc.*—Indistinct at this stage.
*Receptacle height.*—0.3 cm.
*Receptacle diameter.*—0.3 cm.

Ray florets:
*Average quantity of florets.*—About 100 in several whorls.
*Color of florets, upper surface.*—RHS 6B becoming more overlaid with maturity with muted hues of RHS 34C to RHS 34D in slight striations — more on the upper half of petal.
*Lower surface.*—RHS 8C and a little darker at the apex.
*Length.*—2.4-2.7 cm.
*Width.*—0.6-0.7 cm.
*Shape.*—Oblong.
*Apex shape.*—Praemorse.
*Margin.*—Entire.
*Texture, upper surface.*—Papillose.
*Lower surface.*—Papillose.

Disc florets:
*Average quantity of florets.*—About 6.
*Color of florets.*—RHS 1C with RHS 6A apex.
*Length.*—0.3-0.35 cm.
*Width.*—0.1 cm.
*Shape.*—Tubular, elongated.
*Apex shape.*—Acute, 5 pointed.

Phyllaries:
*Quantity.*—About 20-25.
*Color, upper surface.*—RHS 137B.
*Lower surface.*—RHS 137B but appears lighter grey due to hairs.
*Length.*—0.6-0.7 cm.
*Width.*—0.2-0.25 cm.
*Shape.*—Lanceolate.
*Apex shape.*—Acute.
*Base.*—Fused.
*Margins.*—Entire, some papery.
*Texture, upper surface.*—Glabrous.
*Lower surface.*—Bifid T-shaped hairs.

Reproductive organs:
*Pistil.*—1, found on both types of florets.
*Length.*—0.4-0.45 cm.
*Style color.*—RHS 1C.
*Style length.*—0.35-0.4 cm.
*Stigma color.*—RHS 9B.
*Stigma shape.*—Bi-parted.
*Ovary color.*—RHS 155C.
*Ovary length.*—0.075 cm.
*Ovary width.*—0.1 cm.
*Stamens.*—4, found on only on the disc florets.
*Color of filaments.*—RHS 1C.
*Length filaments.*—0.2 cm.
*Anther color.*—RHS 16A.
*Anther length.*—0.1 cm.
*Anther shape.*—Oblong.
*Color of pollen.*—RHS 17B.
*Pollen amount.*—Abundant.

What is claimed is:

1. A new and distinct variety of *Chrysanthemum* plant named 'CIFZ0024' substantially as illustrated and described herein.

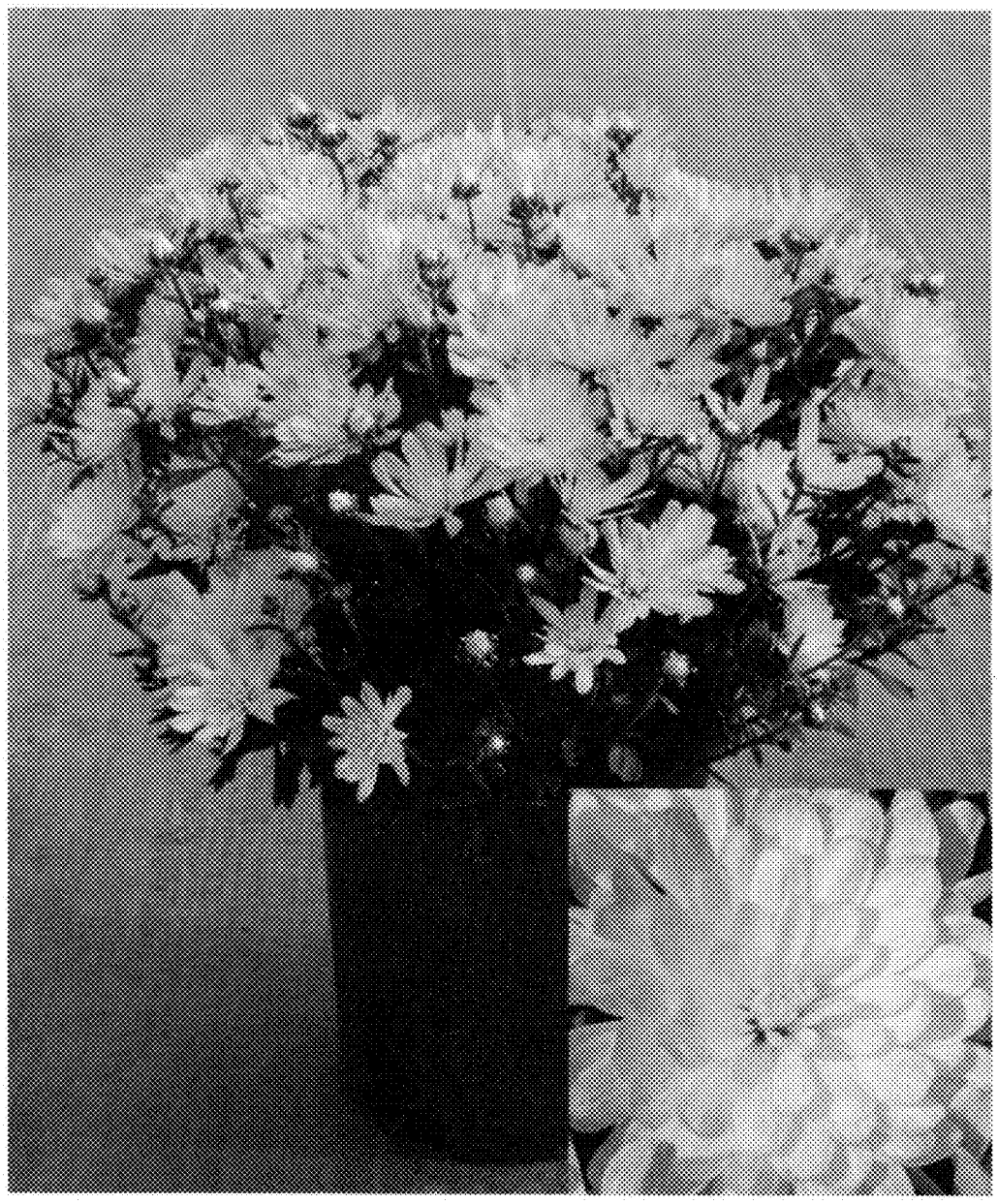

* * * * *